(12) United States Patent
Yamaoka et al.

(10) Patent No.: US 8,273,717 B2
(45) Date of Patent: Sep. 25, 2012

(54) INHIBITOR FOR PERIOPERATIVE BLOOD SUGAR ELEVATION

(75) Inventors: Ippei Yamaoka, Tokushima (JP); Yasuhiro Mitsumoto, Naruto (JP); Masako Doi, Naruto (JP); Tetsuya Fukunaga, Naruto (JP); Mitsuo Nakayama, Naruto (JP)

(73) Assignee: Otsuka Pharmaceutical Factory, Inc., Tokushima (JP)

( * ) Notice: Subject to any disclaimer, the term of this patent is extended or adjusted under 35 U.S.C. 154(b) by 1185 days.

(21) Appl. No.: 10/542,660

(22) PCT Filed: Feb. 5, 2004

(86) PCT No.: PCT/JP2004/001227
§ 371 (c)(1),
(2), (4) Date: Dec. 23, 2005

(87) PCT Pub. No.: WO2004/069236
PCT Pub. Date: Aug. 19, 2004

(65) Prior Publication Data
US 2006/0116426 A1     Jun. 1, 2006

(30) Foreign Application Priority Data

Feb. 6, 2003   (JP) .................................. 2003-029260
Aug. 8, 2003   (JP) .................................. 2003-290792

(51) Int. Cl.
*A61K 31/7004*   (2006.01)
*A61K 31/70*     (2006.01)
*A61K 31/195*    (2006.01)

(52) U.S. Cl. ......................................... 514/23; 514/561
(58) Field of Classification Search ................... 514/23, 514/561
See application file for complete search history.

(56) References Cited

U.S. PATENT DOCUMENTS

| 6,008,256 A | 12/1999 | Haraguchi et al. |
| 2004/0253227 A1 | 12/2004 | Martin et al. |

FOREIGN PATENT DOCUMENTS

| JP | 60-255722 | | 12/1985 |
| JP | 61-30523 | | 2/1986 |
| WO | 85/03872 | | 9/1985 |
| WO | WO 85/03872 | * | 9/1985 |
| WO | 91/18610 | | 12/1991 |
| WO | 96/18313 | | 6/1996 |
| WO | 02/069964 | | 9/2002 |
| WO | 02/078676 | | 10/2002 |

OTHER PUBLICATIONS

Kasai et al. (British Journal of Anaesthesia, vol. 90, No. 1, 2003, 58-61).*
Lucas et al. (Journal of Clinical Investigation vol. 42, No. 2, 1963, pp. 230-238).*
Okita et al. (Journal of Nutrition 114 (7), 1985, pp. 1235-1241).*
Pinter (XP002477225, vol. 3, 1973, 149-162, Database EMBASE [Online], Database Accession No. EMB-0008745430, abstract).*
Saitoh et al. (Tohoku Journal of Experimental Medicine, vol. 129, No. 3, pp. 257-272, Nov. 3, 1979).*
Johansen et al. (Laboratory Animals (1994) 28, 244-248).*
Sugawara et al., "Tonyobyo Kanja no Shujutsuki Kanri", Journal of Clinical Anesthesia, vol. 23, No. 3, pp. 507-514, 1999, (Abstract).
Clinical Observation of Blood Glucose Perioperation in CPB Children, the Journal of Nursing Science, Aug. 2002, vol. 17, No. 8, p. 566 (Abstract in English).
Office Action dated May 12, 2010 for corresponding European patent application 04 708 506.3-2123.
Metrot et al., "Blood Glucose and Propofol in Outpatient Anesthesia," Ambulatory Surgery, vol. 1, pp. 101-102 (1993).
Database EMBASE [Online], G.A. Zampa et al., "Pancreatic Insulinomas Responsive to 1-Leucine: Investigation of Carbohydrate Metabolism in Two Cases Before and After Surgery", XP002477224, Database Accession No. EMB-0008643686, abstract. Giornale Di Clinica Medica 1965, vol. 46 No. 8, 615-642.
C. F. Deacon et al., "GLP-1-(9-36) Amide Reduces Blood Glucose in Anesthetized Pigs by a Mechanism that does not Involve Insulin Secretion", American Journal of Physiology Endocrinology and Metabolism, American Physiological Society, vol. 282, pp. E873-E879, Apr. 2002.
Y. Saitoh et al., "Effects of Eight Amino Acids on the Exocrine and Endocrine Pancreatic Function", Tohoku Journal of Experimental Medicine, vol. 129, No. 3, pp. 257-272, Nov. 3, 1979.
T. Schricker et al., "Integrated Analysis of Protein and Glucose Metabolism During Surgery: Effects of Anesthesia", Journal of Applied Physiology, vol. 91, No. 6, pp. 2523-2530, Dec. 2001.
Z Kinderchir und Grenz 12:149-162, 1973 Database EMBASE [Online], A. Pinter, "The Metabolic Effects of Anaesthesia and Surgery in the Newborn Infant. Changes in the Blood Levels of Glucose, Plasma Free Fatty Acids, α Amino Nitrogen, Plasma Amino Acid Ratio and Lactate in the Neonate", XP002477225, Database Accession No. EMB-0008745430, abstract.
R. H. Bower et al., "Branched Chain Amino Acid-Enriched Solutions in the Septic Patient", Annals of Surgery, vol. 203, No. 1, pp. 13-20, Jan. 1986.
T. W. Mattox et al., "Brief Communication: Clinical Experience with High Branched-Chain Parenteral Nutrition", Journal of the American College of Nutrition, vol. 11, No. 1, pp. 25-28, 1992.
European Office Action issued May 9, 2012 in corresponding European Application No. 04 708 506.3.
Dal Santo, Gianfranco, "A Laboratory Basis for Anesthesiology: Anesthesia and Endocrine Pancreas", pp. 589-611, Piccin Nuova Libraria S.p.A., 1993, XP009158242.

* cited by examiner

*Primary Examiner* — Shaojia Anna Jiang
*Assistant Examiner* — Michael C Henry
(74) *Attorney, Agent, or Firm* — Wenderoth, Lind & Ponack, L.L.P.

(57) ABSTRACT

An inhibitor for perioperative blood sugar elevation characterized by containing a branched amino acid, a compound which can be converted into a branched amino acid in vivo or a compound to which an amino group has been transferred from a branched amino acid. This inhibitor for perioperative blood sugar elevation is useful as a drug which is safe to the living body including human, inhibits abnormal elevation in the blood glucose level caused by anesthesia, surgery, etc., and enables proper blood sugar control, when administered to a perioperative patient.

2 Claims, 5 Drawing Sheets

US 8,273,717 B2

INHIBITOR FOR PERIOPERATIVE BLOOD SUGAR ELEVATION

This application is a U.S. national stage of International Application No. PCT/JP2004/001227 filed Feb. 5, 2004.

TECHNICAL FIELD

The present invention relates to a drug which inhibits blood sugar elevation caused by stress of perioperative anesthesia, surgery, etc., which is characterized by containing a branched amino acid.

BACKGROUND ART

It is generally known that when a living body including human patient receives invasive stress caused by, for example, anesthesia, surgery, or the like which is a factor affecting homeostasis in vivo, the living body leads to secrete various insulin's antagonistic hormones (catecholamine, glucagon, corticoid, etc.), promotes gluconeogenesis and glycogenolysis in the liver, and elevates the blood glucose (hereinafter, also referred to as blood sugar) level through autonomic nervous system/endocrine system in order to maintain the function of living cells (for example, see MAYUMI et al., "IGAKU NO AYUMI", Vol. 168, pages 418-423, 1994).

In particular, dehydration may be occurred due to significant hyperglycemia or osmotic diuresis in patients with sugar metabolism disorders such as diabetes mellitus in the perioperative period, because of insufficient insulin action resulting from nearly fasting conditions or invasive stress, etc. caused by anesthesia or surgery, etc. If these conditions will continue, severe complications such as abnormal metabolism, coma, and multiple organ failure may sometimes occur in the patients because of severe insufficiency in sugar utilization. In the case of these patients, when the patients in the perioperative period are given no sugar, body proteolysis and lipolysis occur, free fatty acids and ketone bodies are increased in the blood, resulting in ketoacidosis. This can occur not only in the patients with sugar metabolism disorder, but also similarly in the patients who undergo highly invasive surgery required for a long operation time or in the patients with severe diseases which are treated intensively at ICU, etc.

Accordingly, control of blood sugar level in the perioperative period is an important issue under the management of general anesthesia. It is known that the management of blood sugar level in the perioperative period within the appropriate range leads not only to shorten the period required for curing after surgery but also to increase the probability of survival for patients after surgery.

Presently, control of blood sugar level in the perioperative period is performed by supplementation of saccharides, usually glucose, and by insulin administration method in the case of hyperglycemia. The insulin administration method is a method of continuous intravenous administration of insulin by using an infusion pump while monitoring the patient's blood sugar level and serum insulin concentration of patients, if required, after the surgery, in order to keep the level within an appropriate range during the surgery.

However, continuous control of correct insulin dosage for patients requires advanced technique. When insulin is excessively administered by mistake, the patient becomes hypoglycemia and has a risk of causing coma or severe damage in central nervous system. In normal surgery, in order to maintain body's protein and fat and to prevent ketoacidosis, infusion such as saccharides is supplied to the patient, and the insulin dosage depends on these supplied saccharides, and thus more advanced control thereof is required. In addition, with respect to the patient whose insulin sensitivity is decreased, such as insulin-independent diabetes mellitus observed frequently in elderly people or overweight people, the effect on blood sugar level reduction by the above-mentioned insulin administration is not sometimes expected enough.

Hence, the control technique of blood sugar level by insulin administration is not necessarily a safe method for patients, and the control/management is difficult.

Therefore, like an inhibitor for blood sugar elevation of the present invention, the inhibitor for blood sugar elevation which is safe for patients has never been known yet at the point that the constituent components contains branched amino acids. In addition, it can be said that the present invention is an excellent invention, because strict control of the insulin dosage is not necessarily needed unlike the insulin administration method, and the supplementation of saccharides can be easily performed in the perioperative period.

DISCLOSURE OF THE INVENTION

It is an object of the present invention to provide a drug which inhibits blood sugar elevation observed in the perioperative period, more particularly to provide an inhibitor for blood sugar elevation, which is safe to the living body including human patient and inhibits abnormal elevation of the blood sugar level observed in the perioperative period by administering to patients under anesthesia.

The inventors have focused attention on amino acids as a compound which affects homeostasis in vivo and is safe to the living body. In order to solve the above-mentioned problem, the inventors of this invention have found the present invention by studying physiological function of amino acids under anesthesia which affects homeostasis in vivo compared to under non-anesthesia. Specifically, the present inventors have found that when administered an amino acid infusion containing essential, semi essential, and non-essential amino acids to rats operated under anesthesia, the blood sugar level of rats under anesthesia is more decreased than that of rats under non-anesthesia. In addition, the present inventors have studied extensively and have found that a branched amino acid has an effect to inhibit blood sugar elevation in the above living body among these amino acids contained in amino acid infusion and that in the perioperative period, in particular under anesthesia, the inhibiting effect is increased, i.e. the effective dosage of amino acids to exert the action is also lower than under non-anesthesia. The inventors have found that when glucose and these amino acids are administered at the same time under administering anesthetic agent, insulin secretion is more facilitated than under non-anesthesia. The present inventors have reached the completion of the present invention by studying extensively based on these findings.

That is, the present invention relates to:
(1) An inhibitor for perioperative blood sugar elevation, which is characterized by containing a branched amino acid, a compound which can be converted into a branched amino acid in vivo, or a compound to which an amino group is transferred from a branched amino acid,
(2) The inhibitor for blood sugar elevation according to the above (1), wherein the branched amino acid is leucine and/or isoleucine,
(3) The inhibitor for blood sugar elevation according to the above (1) or (2), wherein the compound which can be converted into a branched amino acid in vivo is a salt, an ester, or an amide of a branched amino acid, or an oligopeptide containing a branched amino acid, (4) The inhibitor for blood sugar elevation according to the above (1), wherein the compound to which an amino group is transferred from a branched amino acid is α-ketoisocaproic acid or α-keto-β-methylvaleric acid, (5) The inhibitor for blood sugar elevation according to any one of the above (1) to (4), which contains 0.25 to 2.5 g/dL of leucine and/or 0.25 to 3.5 g/dL of isoleucine, (6) The inhibitor for blood sugar elevation according to any one of the above (1) to (4), which contains 1 to 10 g/dL of glucose and 0.25 to 2.5 g/dL of leucine and/or 0.25 to 3.5 g/dL of isoleucine, (7) The inhibitor for blood sugar elevation according to any one of the above (1) to (6), wherein the blood sugar elevation is caused by an anesthetic agent, (8) The inhibitor for blood sugar elevation according to any one of the above (1) to (6), which is used for treating and/or preventing blood sugar elevation under anesthesia, (9) The inhibitor for blood sugar elevation according to any one of the above (1) to (6), which is used in combination with an anesthetic agent,

(10) A method of inhibiting blood sugar elevation, which comprises administering the inhibitor for blood sugar elevation according to any one of the above (1) to (6), to a perioperative patient,

(11) A method of anesthetizing, which comprises using an anesthetic agent in combination with the inhibitor for blood sugar elevation according to any one of the above (1) to (6),

(12) Use of a branched amino acid, a compound which can be converted into a branched amino acid in vivo, or a compound to which an amino group is transferred from a branched amino acid for preparing a drug inhibiting blood sugar elevation in a perioperative patient, and

(13) Use of a branched amino acid, a compound which can be converted into a branched amino acid in vivo, or a compound to which an amino group is transferred from a branched amino acid for preparing a drug inhibiting blood sugar elevation caused by an anesthetic agent.

In the present invention, the "perioperative period" means a period of before surgery, during operation under operative invasion caused by surgery/anesthesia, and after surgery.

BEST MODE FOR CARRYING OUT THE INVENTION

Figure 1:
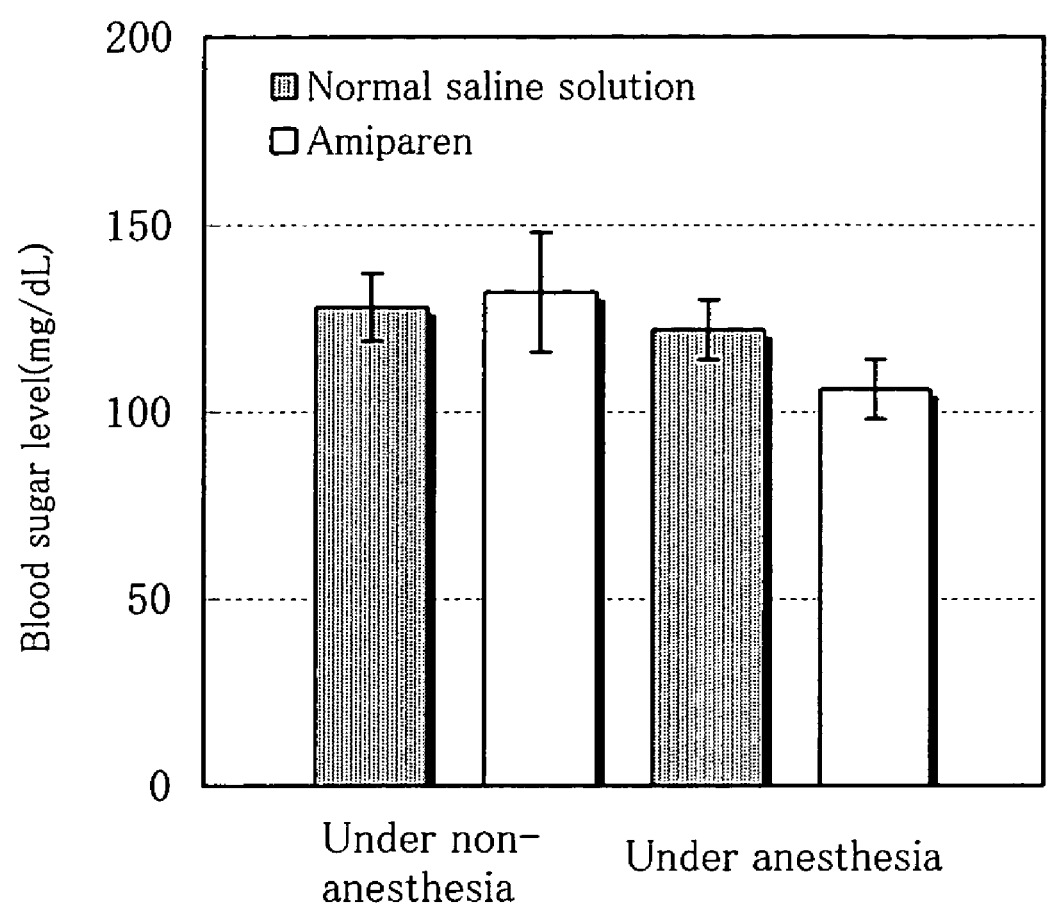
FIG. 1 shows an examination result of the effect of amino acids on blood sugar level by parallel administration to rats under non-anesthesia or anesthesia.

The above-mentioned amino acids (hereinafter, abbreviated as BCAA) are not particularly limited, so long as they meet the standards described in The Japanese Pharmacopoeia, including any amino acids, such as L-amino acids, D-amino acids, α-amino acids, β-amino acids, γ-amino acids, natural amino acids, synthetic amino acids and the like, preferably natural L-amino acids or α-amino acids. In addition, the above-mentioned amino acids may be prepared by hydrolyzing plant-derived or animal-derived proteins with the use of protease, or by microbial fermentation method, or may be synthetic amino acids which are prepared by introducing amino groups into organic acids, etc.

BCAA is preferably leucine, isoleucine, or valine.

These amino acids may be used solely or in combination thereof. Specifically, there is exemplified (a) leucine alone, (b) isoleucine alone, (c) a mixture of leucine and isoleucine, (d) a mixture of leucine and valine, (e) a mixture of isoleucine and valine, or (f) a mixture of leucine, isoleucine and valine.

A compound which is convertible into the above-mentioned BCAA in vivo may be a pharmaceutically acceptable salt thereof with acid or base, specifically, an acid addition salt or a base addition salt of BCAA (e.g. sodium salt, potassium salt, hydrochloride, acetate, etc.), an ester thereof (e.g. methyl ester, ethyl ester, propyl ester, etc.), or an amide thereof (e.g. amide, monomethyl amide, monoethyl amide, dimethyl amide, diethyl amide, etc.).

In addition, the compound which is convertible into the above-mentioned BCAA in vivo may be an analog of BCAA, which is a precursor of BCAA, for example, oligopeptides comprising BCAA as constituent elements, and the like. As for such oligopeptides, for example, there is exemplified a dipeptide such as L-isoleucyl-L-leucine, L-leucyl-L-alanine, and the like. These analogs may be alone or in a mixture thereof.

A compound to which an amino group is transferred from BCAA may be a compound prepared by that an amino group of BCAA transfers to amino group receptor such as α-ketoglutaric acid (2-oxoglutaric acid) by aminotransferase. For example, the compound to which an amino group is transferred from each of leucine, isoleucine or valine is, for example, α-ketoisocaproic acid, α-keto-β-methylvaleric acid, or α-ketoisovaleric acid, respectively.

BCAA, a compound which can be converted into the above-mentioned BCAA in vivo, and a compound to which an amino group is transferred from BCAA may be crystalline or may be non-crystalline.

There is no particular limitation to a mixing amount of BCAA or a compound which can be converted into the above-mentioned BCAA in vivo, contained in an inhibitor for blood sugar elevation provided the above-mentioned inhibitor is within the range that it is retained stably without crystal precipitation even in the case of long time storage, preferably within the following range.

For example, when the above-mentioned inhibitor is a liquid agent and BCAA contained is alone, e.g., in the case (a) leucine alone or (b) isoleucine alone, each BCAA concentration is preferably about 0.5 to 4.0 g/dL, more preferably about 0.7 to 3.0 g/dL. When BCAA contained in the above-mentioned inhibitor is a mixture, for example, each mixing weight ratio of (c) mixture of leucine and isoleucine, (d) mixture of leucine and valine, (e) mixture of isoleucine and valine, or (f)

mixture of leucine, isoleucine and valine is (c) leucine:isoleucine=about 1:about 0.25 to 4, (d) or (e) leucine or isoleucine:valine=about 1:about 0.25 to 4, or (f) leucine:isoleucine:valine=about 1:about 0.25 to 4:about 0.25 to 1, and it is preferable that each BCAA concentration is within the above-mentioned range.

Since it is preferable that an inhibitor for blood sugar elevation of the present invention is administered to the living body (patient) by direct intravenous, and continuous infusion via intravenous drip, etc. in the perioperative period, the dosage form thereof is preferably a liquid agent such as an injectable solution for an intravenous drip, and may be a granule preparation or a powder preparation of the freeze-dried product which is used just before administration by dissolving it in the distilled water for injection etc. when used. In addition, those preparations can be administered orally prior to surgery, and the effect continues until the intraoperative period when a patient is under anesthesia.

The preparation method may be subjected to the known preparation technique of amino acid infusions or amino acid preparations. This is done in such a manner that the above-mentioned constituting components is usually dissolved and mixed in distilled water for injection, and if required, an additive, etc. is added thereto. Then, the resulting aqueous solution is subjected to removal of bacteria with a filter, etc. or sterilized under heating, etc. and formulated into a liquid agent.

The inhibitor for blood sugar elevation of the present invention may be mixed with various kinds of additives depending on the necessity in order to stabilize the above-mentioned inhibitor, etc. Examples of such additives specifically include a pH adjusting agent such as hydrochloric acid, acetic acid, malic acid, citric acid, sodium hydroxide, and potassium hydroxide, and an osmotic pressure adjusting agent such as Conclyte-Na in order to correct the osmotic pressure of the above-mentioned inhibitor.

The inhibitor for blood sugar elevation of the present invention may contain other components which are known to be usually added to and mixed with amino acid infusions, etc. including, for example, free amino acids such as basic amino acids (e.g. lysine, arginine, etc.) and aromatic amino acids (e.g. tryptophan, phenylalanine, etc.) other than BCAA, or salts thereof, lipids, vitamins, electrolytes, trace elements, and the like. The amount of these components to be added is within the range that the object of the present invention is not inhibited.

When the inhibitor for blood sugar elevation of the present invention is administered to the perioperative living body (patient), blood sugar elevation observed in the perioperative period can be avoided and thus the supplementation of saccharides which are conventionally needed for parallel use of insulin can be performed while inhibiting blood sugar abnormal elevation.

The perioperative living body (patient) is usually under anesthesia and the inhibitor for blood sugar elevation of the present application of the invention can be used advantageously under both general anesthesia and local anesthesia. The anesthesia methods for a patient to be under anesthesia are usually subject to the methods used in the medical field. For example, such methods are inhalational anesthesia, intravenous anesthesia, spinal anesthesia, epidural anesthesia, and the like. In addition, there is no particular limitation for the anesthesia agent which can be utilized in using the inhibitor for blood sugar elevation, examples of the inhalational anesthetic agent are nitrous oxide, anesthetic ether, Isoflurane, Enflurane, Sevoflurane, and Halothane, etc.; examples of the intravenous anesthetic agent are Amobarbital Sodium, Thiamylal Sodium, Thiopental Sodium, Pentobarbital Calcium, Propofol, Benzodiazepine, Diazepam, Midazolam, Hydroxyzine, Droperidol, Fumazenil, Ketamine, etc.; and examples of the local anesthetic agent are Dibucaine Hydrochloride, Mepivacaine Hydrochloride, Procaine Hydrochloride, Ropivacaine Hydrochloride, Anesthamine, Ethyl Aminobenzoate, Lidocaine, Oxethazaine, Tetracaine Hydrochloride, Oxybuprocaine Hydrochloride, Bupivacaine Hydrochloride, etc. (refer to therapeutic category described in The Japanese Pharmacopoeia, Fourteenth Edition, etc.)

It is preferable that the inhibitor for blood sugar elevation of the present invention is continuously administered intravenously to the living body (patient) in the case of liquid agent as it is, and in the case of freeze-dried product after it is dissolved in sterile distilled water when used. With respect to the administration rate, the optimal rate is adopted in each case by considering body weight of the living body (patient) to be administered and BCAA concentration, etc. in the above-mentioned inhibitor, and in addition it is preferable that in the operative period the rate is adjusted timely by medical doctor with monitoring the blood sugar level, so that it is not necessarily appropriate to suggest the rate. Generally, total BCAA quantity is about 2 to 200 mg/body weight-kg/time, preferably 5 to 500 mg/body weight-kg/time. In the case of oral agent, 5 to 300 mg/body weight-kg is administered orally before administration of an anesthetic agent.

EXAMPLES

In the present invention, preferably preparation examples and test examples are illustrated as below and the invention, however, should not be limited to the following preparation examples, etc.

Each abbreviation illustrated in the present description and drawings etc. is shown below. In addition, amino acids are regarded as L-amino acids when there are optical isomers, unless otherewise specifically stated.
BCAA: branched chain amino acid
EAA: essential and semi-essential amino acid
Leu: leucine
Ile: isoleucine
Val: valine
Lys: lysine
Thr: threonine
Trp: tryptophan
Met: methionine
Phe: phenylalanine
Cys: cysteine
Tyr: tyrosine
Arg: arginine
His: histidine
Ala: alanine
Pro: proline
Ser: serine
Asp: aspartic acid
Glu: glutamic acid
Glucose: glucose Reference Example Aqueous amino acid solutions described in Reference Examples 2 to 6 are prepared (refer to Table 1). In addition, Reference Example 1 relates to an amino acid infusion "Amiparen" (10% general amino acid infusion) manufactured by OTSUKA PHARMACEUTICAL FACTORY, Inc. Reference Example 2 relates to an amino acid solution containing essential and semi-essential amino acids (EAA) only among amino acids contained in Reference Example 1. Reference Example 3, 4, 5, or 6 relates to an amino acid solution containing the residual amino acids removed from BCAA, basic amino acids, aromatic amino acids, or other amino acids, respectively.

As for each amino acid, freeze-dried products (manufactured by AJINOMOTO Co. Ltd., KYOWA HAKKO KOGYO Co. Ltd., etc.) are used. Each amino acid was added to 450 mL of distilled water for injection so as to be a concentration described in Table 1, and dissolved while stirring with a stirrer. In addition, when the osmotic pressure ratio to normal saline solution was less than 1, Conclyte-Na was added to correct the osmotic pressure so that the solution was made isotonic to blood fluid. The pH of the solution is adjusted within the range of 6.5 to 7.4 with glacial acetic acid, 500 mL of the aqueous solution was measured, and the solution was sterilized by heat (106° C., 32 min.) to prepare each amino acid solution of Reference Examples 2 to 6.

TABLE 1

| | Reference Example | | | | | |
|---|---|---|---|---|---|---|
| | 1 General | 2 EAA | 3 -BCAA | 4 -Base | 5 -Aromatic | 6 -Other |
| L-Leu | 1.40 | 1.40 | | 1.40 | 1.40 | 1.40 |
| L-Ile | 0.8 | 0.8 | | 0.8 | 0.8 | 0.8 |
| L-Val | 0.8 | 0.8 | | 0.8 | 0.8 | 0.8 |
| L-Lys acetate | 1.05 | 1.05 | 1.05 | | 1.05 | 1.05 |
| L-Thr | 0.57 | 0.57 | 0.57 | 0.57 | 0.57 | |
| L-Trp | 0.2 | 0.2 | 0.2 | 0.2 | | 0.2 |
| L-Met | 0.39 | 0.39 | 0.39 | 0.39 | 0.39 | |
| L-Phe | 0.7 | 0.7 | 0.7 | 0.7 | | 0.7 |
| L-Cys | 0.1 | | | | | |
| L-Tyr | 0.05 | | | | | |
| L-Arg | 1.05 | 1.05 | 1.05 | | 1.05 | 1.05 |
| L-His | 0.5 | 0.5 | 0.5 | | 0.5 | 0.5 |
| L-Ala | 0.8 | | | | | |
| L-Pro | 0.5 | | | | | |
| L-Ser | 0.3 | | | | | |
| Aminoacetic acid | 0.59 | | | | | |
| L-Asp | 0.1 | | | | | |
| L-Glu | 0.1 | | | | | |
| Total | 10.00 | 7.46 | 4.46 | 4.86 | 6.56 | 6.5 |

(g/100 ml)

Preparation Examples

The amino acids solutions of Preparation Examples 1 to 5 described in Table 2 were prepared in a similar method to Reference Examples.

TABLE 2

| | Preparation Example (g/100 mL) | | | | |
|---|---|---|---|---|---|
| | 1 | 2 | 3 | 4 | 5 |
| L-Leu | 1.40 | 2.00 | | 1.00 | |
| L-Ile | 0.8 | | 2.00 | 1.00 | |
| L-Val | 0.8 | | | | 2.00 |
| Total | 3.00 | 2.00 | 2.00 | 2.00 | 2.00 |

Test Example 1

Effect of Amino Acid Administration on Blood Sugar Level in Rats Under Non-Anesthesia or Anesthesia On the day before the test, a rat cervical portion was incised under ether anesthesia, and each catheter for anesthetic agent administration and for aqueous amino acid solution administration was kept in the right external jugular vein. After the rat was fixed to a harness, the other end of catheter running subcutaneously was exposed from the rat backside, and was connected to the swivel via the harness to be fixed. A normal saline solution (Saline) was administered continuously at the rate of 1 mL/hr/body through the catheter for aqueous amino acid solution administration until just before the test. Thereafter, the rat was fed under the fasting condition, permitting the rat to take drinking water freely.

On the day of the test, the rat was transferred to a room with acoustical and electronic insulation. Then, each catheter was connected via a branched connector to a cable for polygraph and a syringe pump for administration of anesthetic agent or for administration of aqueous amino acid solution (anesthetic agent: micro syringe pump type EP32, manufactured by EICOM Corp., aqueous amino acid solution: JMS syringe pump type SP100 s). After bioelectric potential (EEG, EMG, body temperature, biovibration) of the rat was preliminarily ascertained to be stable for 1 hour, the bioelectric potential was further recorded for 30 minutes until just before the anesthesia was started. The procedure so far was considered as pre-treatment, and the following Test Examples was also subjected thereto.

To the anesthetic administration group (n=16), a bolus of 15 mg/kg of Propofol (Diprivan 1%, Zeneca S.p.A., Italy) was administered intravenously, and 45 mg/kg/hr (i.v.) of Propofol was intravenously administered continuously for 30 minutes, and then 22.5 mg/kg/hr (i.v.) thereof for 2.5 hours.

To the anesthetic non-administration group (n=16), a bolus of 1.5 mL/kg (i.v.) of Intralipos (lipid emulsion for intravenous injection, manufactured by OTSUKA PHARMACEUTICAL FACTORY, Inc.) was administered intravenously, and then Intralipos was intravenously administered continuously for total 3 hours similarly to the anesthetic administration group.

"Amiparen" (n=8) of Reference Example 1 (manufactured by OTSUKA PHARMACEUTICAL FACTORY, Inc.) described in Table 1 or a normal saline solution (n=8) was intravenously administered continuously to rats of both groups at the rate of 14 mL/kg/hr through the catheter for aqueous amino acid solution administration in parallel with Propofol administration or Intralipos administration.

Just after the end of the administration of the solution in Reference Example 1 and an anesthetic agent, Pentobarbital Na (50 mg/kg) was administered to rats of both groups through the catheter for aqueous amino acid solution administration group, and blood was collected from the abdominal aorta. The blood sugar level was determined by enzymatic method (Glucose-DH Method). In addition, comparison between both groups was performed by testing the difference between the normal saline solution administration group and the aqueous amino acid solution administration group after two-way analysis of variance was performed (t test).

The result of Test Example 1 is shown in FIG. 1. With respect to the anesthetic administration group, significant decrease of the blood sugar level in the Amiparen (Reference Example 1) parallel administration group was observed, suggesting that, under anesthesia, amino acids administration is effective to inhibit blood sugar elevation by the surgical stress.

Test Example 2

Identification of kinds of amino acids having an inhibiting effect on blood sugar elevation A test was performed on which amino acids have an inhibiting effect on blood sugar elevation of amino acids which are contained in Reference Example (Amiparen) used in Test Example 1.

To a rat which was pre-treated in a similar manner to Test Example 1 was administered intravenously a bolus of 15 mg/kg of Propofol, and then Propofol was intravenously administered continuously for 3 hours according to Test Example 1. To the above-mentioned rat was administered each aqueous amino acid solution of References 2 to 6 (each administration group n=8) or normal saline solution (control group n=8) intravenously at the rate of 14 mL/kg/hr in parallel with Propofol administration. After completion of the administration, blood was collected from the abdominal aorta according to Test Example 1 and then the blood sugar level and the serum insulin value were determined.

The serum insulin value was determined by ELISA Method (manufactured by Mevcodia Co.).

Figure 2:
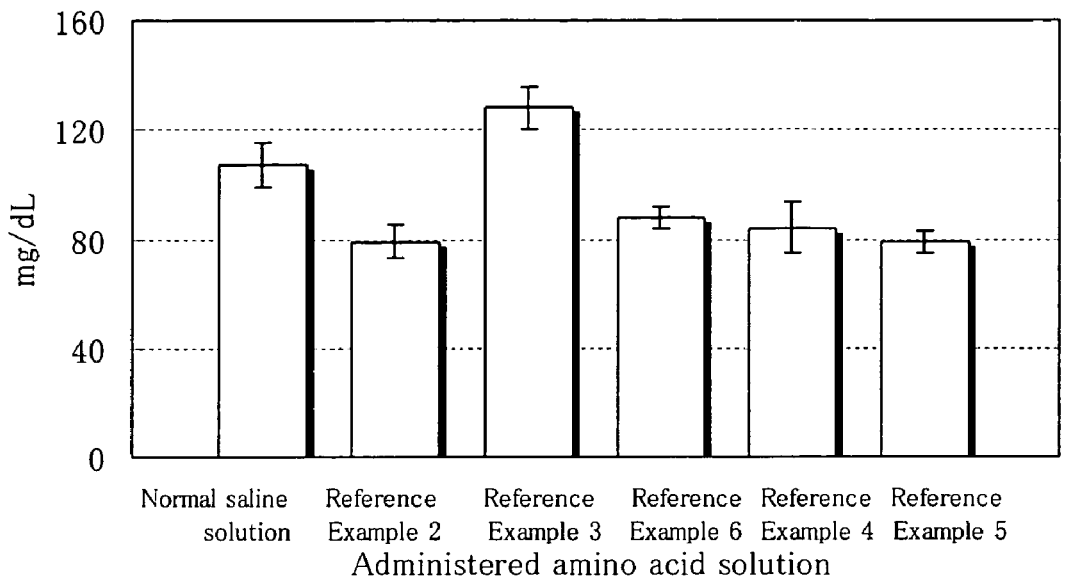
FIG. 2 shows an examination result of the identification of kinds of amino acids having an inhibiting effect on blood sugar elevation.
Figure 2:
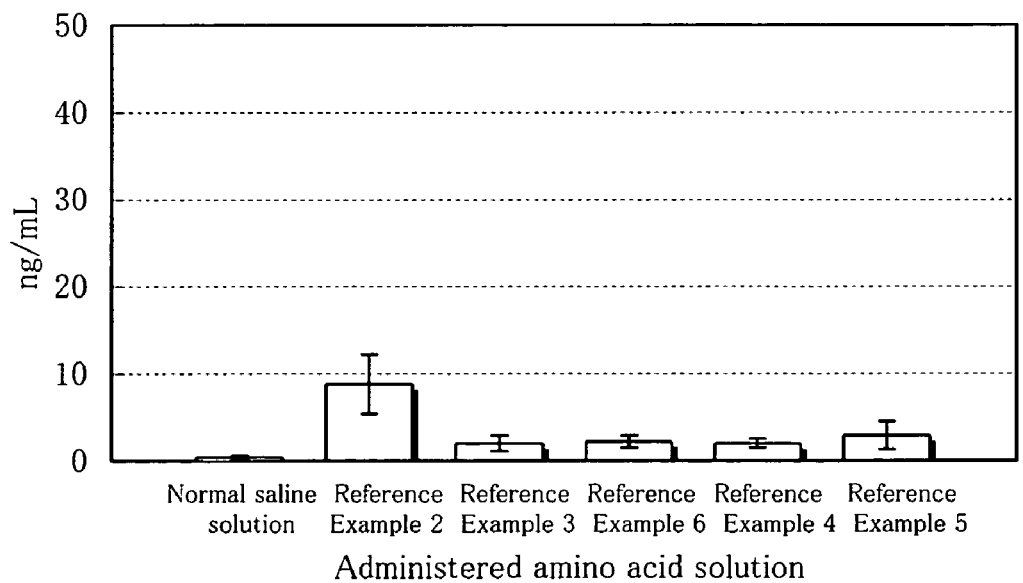

The result of Test Example 2 is shown in FIG. 2. As a result, with respect to aqueous amino acid solution administration groups of References 4 to 6, (A) obvious decrease of blood sugar level was observed in comparison with normal saline solution administration (control group), and the each level was similar to that of the administration groups (Reference Example 2) of aqueous amino acids solution containing essential and semi-essential amino acids. To the contrary, aqueous amino acid solution not containing BCAA administration groups (Reference Example 3) showed high blood sugar level similar to the control group. This result showed that BCAA is effective to inhibit blood sugar elevation.

In addition, with respect to Reference 2 administration group, (B) increase in insulin levels was observed with decrease in blood sugar levels and, with respect to References 4 to 6 administration groups where decrease in blood sugar levels was shown similarly, insulin level increase was a little bit. To the contrary, with respect to Reference 3 administration group, insulin level showed low level similarly to those of the Reference Examples 4 to 6 administration groups.

Test Example 3

Confirmatory Test of Inhibiting Effect on Blood Sugar Elevation by BCAA (3 Kind Mixtures, Leu+Ile+Val)

Based on the result obtained in Test Example 2, confirmatory test of an inhibiting effect on blood sugar elevation by BCAA was performed.

To a rat which was pre-treated similarly to Test Example 1 was administered intravenously a bolus of 15 mg/kg of Propofol, and then Propofol was intravenously administered continuously for 3 hours. Propofol is intravenously administered continuously for 1 hour at the rate of 45 mg/kg/hr (i.v.), and then for 2 hours at the rate of 22.5 mg/kg/hr (i.v.). To the above-mentioned rat was intravenously administered aqueous amino acid solution of Preparation Example 1 or normal saline solution at the rate of 14 mL/kg/hr. After the end of the administration, blood was collected from the abdominal aorta according to Test Example 1, and the blood sugar level was determined.

Figure 3:
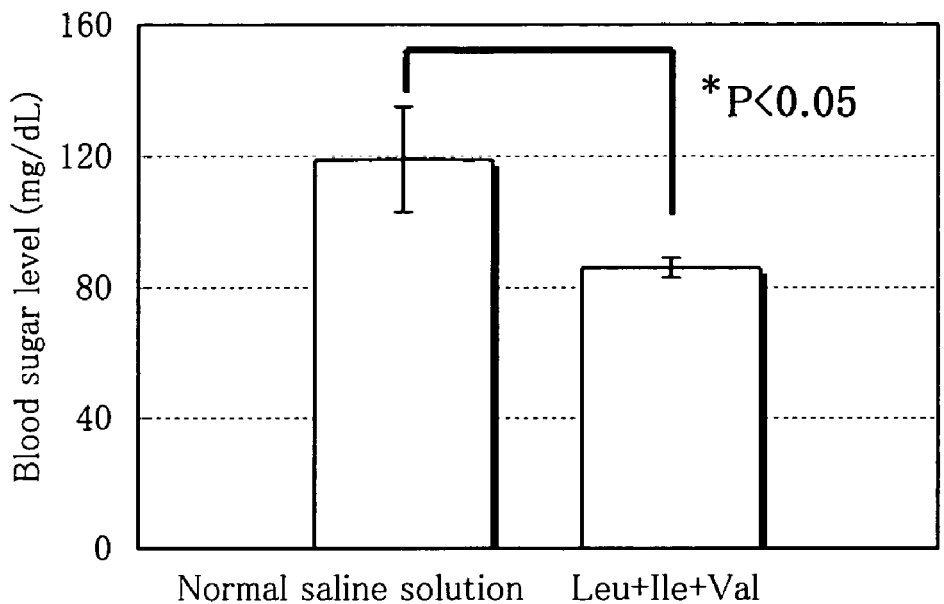
FIG. 3 shows a confirmatory test result of an inhibiting effect on blood sugar elevation by BCAA (3 kind mixtures, Leu+Ile+Val).

The result of Test Example 3 is shown in FIG. 3. With respect to the group to which the aqueous amino acid solution containing 3 kinds of Leu, Ile and Val (Preparation Example 1) was administered, blood sugar level was clearly inhibited compared with the control group. From this result, it was proved that BCAA administration is effective to inhibit blood sugar elevation under anesthesia.

Test Example 4

Identification of Kinds of BCAA Having Inhibiting Effect on Blood Sugar Elevation In addition, investigation was performed on which amino acids, among BCAA, have an inhibiting effect on blood sugar elevation.

Rats were pre-treated similarly to Test Example 1, except that a catheter was kept in the right external tail vein. Instead of Propofol used in the previous tests, after administration of a bolus of Pentobarbital Na (30 mg/kg, i.v., Somnopentyl), Pentobarbital Na was similarly administered continuously for 3 hours at the constant rate of 25 mL/kg/hr via intravenous route. Each aqueous amino acid solution (each administration group n=5) of Preparation Example 2 to 4 or normal saline solution (control group n=5) was administered intravenously at the rate of 14 mL/kg/hr. After the end of the administration, blood was collected from the abdominal aorta and blood sugar level was determined.

Figure 4:
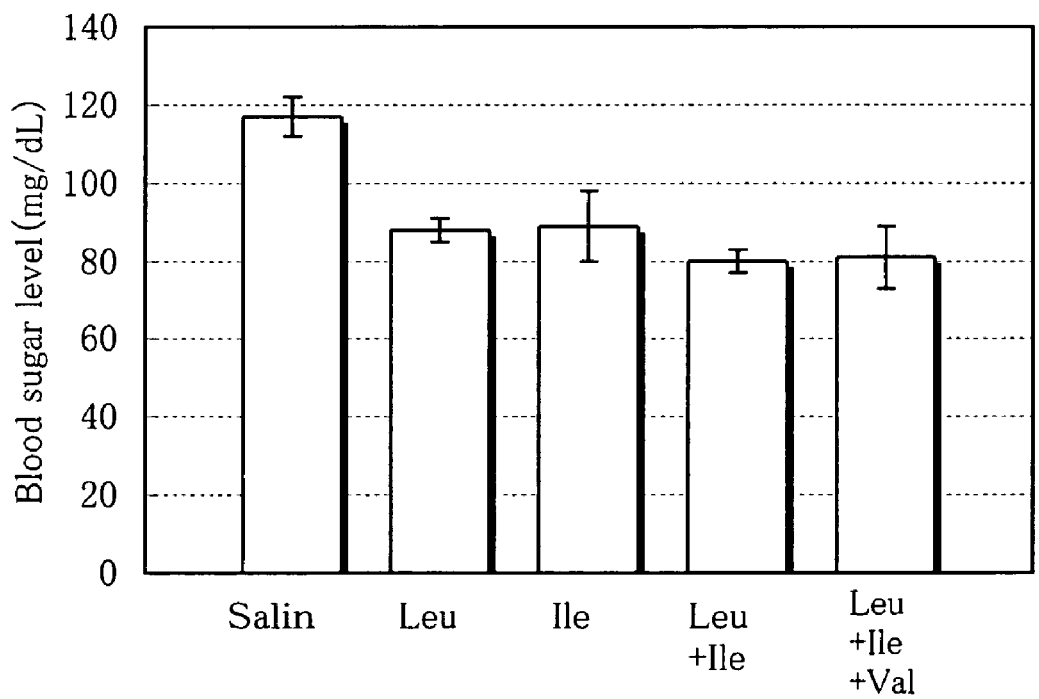
FIG. 4 shows an examination result of the identification of kinds of BCAA having an inhibiting effect on blood sugar elevation.

The result of Test Example 4 is shown in FIG. 4. With respect to each group to which aqueous amino acid solution of Leu alone or Ile alone (Preparation Example 2 or 3), or a mixture of Leu and Ile (Preparation Example 4), blood sugar level was apparently low compared with the normal saline solution administration group (control group), and the level was nearly equal to the group which received 3 kinds of BCAA in Test Example 3. This result revealed that the significant inhibiting effect on blood elevation was also obtained by administration of Leu alone or Ile alone, or a mixture of Leu and Ile under anesthesia. In addition, since Pentobarbital Na was used as an anesthetic agent in this Test Example 4, it was revealed that the inhibiting effect of BCAA on sugar blood elevation was obtained significantly with the use of any anesthetics.

Test Example 5

Examination of Inhibiting Effect on Blood Sugar Elevation by BCAA (3 Kind Mixtures, Leu+Ile+Val)—Parallel Administration Case of Sugar Solution A blood sugar elevation model was made in vivo by intravenous administration of glucose to the living body, and the effect of BCAA parallel administration in the above-mentioned model was examined.

Propofol was administered intravenously to rats which were pre-treated similarly to Test Example 1, continuously for 3 hours according to Test Example 1. To each of the above-mentioned rats was administered intravenously a mixed solution of 50 weight % glucose and 3 kinds mixed solution of BCAA at a ratio of 1:9 (5 weight % glucose+2.7 weight % BCAA:administration group n=6) or 5 weight % aqueous glucose solution alone (control group n=6) at the rate of 14 mL/kg/hr. Blood was collected (100 (L)) through the catheter for aqueous amino acid solution administration before the start of administration, 30 minutes, 90 minutes, and 180 minutes after the start of administration, respectively. And then, the blood sugar level was determined according to Test Example 1.

Figure 5:
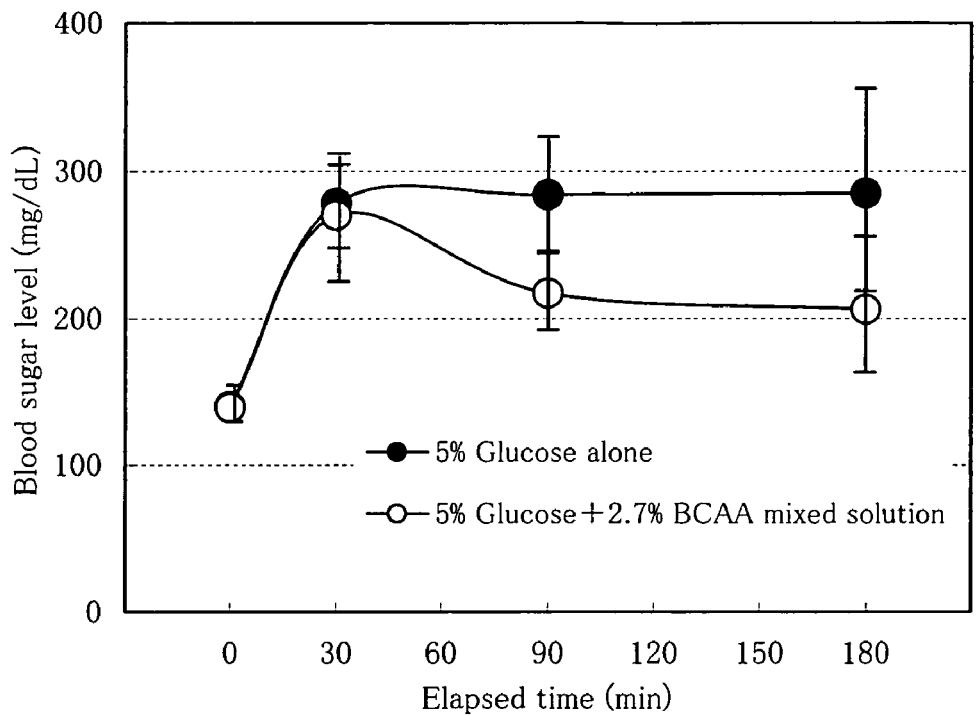
FIG. 5 shows an examination result of an inhibiting effect on blood sugar elevation by BCAA (3 kind mixtures, Leu+Ile+Val) in the case of parallel administration of sugar solution.

The result of Test Example 5 is shown in FIG. 5. In both groups, blood sugar level was apparently increased 30 minutes after the start of administration as compared before the start of administration, and the level had no difference between the both groups. After that, however, in the control group to which 5% aqueous glucose solution was administered, the blood sugar level remained high level (around 280 mg/dL). To the contrary, in the pararell administration group to which 3 kinds mixed solution of BCAA was administered with 5% aqueous glucose solution, the blood sugar level decreased (around 210 mg/dL) 90 minutes after the administration, and thereafter it changed with apparently low level, compared to the control group. This result revealed that the inhibiting effect on blood sugar elevation resulted from the fact that the blood sugar level which was once increased by saccharide supplementation of glucose in the perioperative period was controlled within a proper range of blood sugar level by BCAA of which concentration was increased with the elapse of time after administration.

Test Example 6

Effect of Branched Amino Acids in Blood Sugar Elevation Model by Glucose

A blood sugar elevation model was made by intravenous administration of glucose to the living body, and the effect was examined with parallel administration of leucine, isoleucine and valine in the above-mentioned model.

Rats were pre-treated in a similar manner to Test Example 4, and anesthesia in the rats was maintained for 3 hours by intravenous continuous administration of Pentobarbital in a similar manner to Test Example 4. A mixed solution of 50 weight % glucose and the aqueous solution of Preparation Example 2, 3 or 5 was administered intravenously to each of the above-mentioned rats in a ratio of 1:9 (5 weight % glucose—1.8% each amino acid; n=5), or 5 weight % aqueous glucose solution (n=5) at the rate of 14 mL/kg/hr in parallel with administration of Pentobarbital. Blood was collected (100 µL) through the catheter for administration of aqueous amino acid solution before the start of administration, 30 minutes, 90 minutes, and 180 minutes after the start of administration respectively. And then, the blood sugar level and serum insulin value were determined according to Test Example 1.

Figure 6:
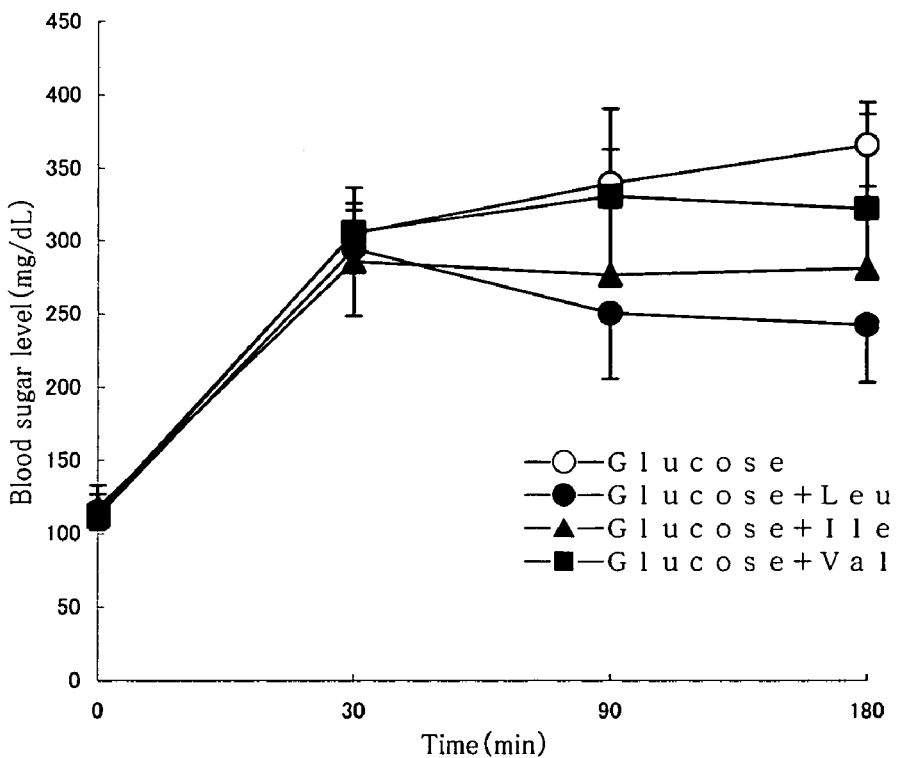
FIG. 6 shows an effect of branched amino acids by continuous infusion of glucose under anesthesia.

The result of Test Example 6 is shown in FIG. 6. The blood sugar level of all groups was approximately 300 mg/dL 30 minutes after the start of test. The blood sugar level of glucose administration group was increased continuously during the determination. The blood sugar level of parallel administration group with leucine reached the maximum 30 minutes after the start of test, after which time the level decreased, and the level became lower significantly compared with glucose administration group 90 and 180 minutes after the start of the test. The blood sugar level of parallel administration group of isoleucine also reached the peak 30 minutes after the start of test, continuous elevation of the blood sugar level was not recognized, and significant difference of the level was recognized compared with glucose administration group 180 minutes after the start of test.

The serum insulin value of parallel administration group of leucine (glucose+leucine) in Test Example 6 is shown in Table 3.

TABLE 3

| | | Serum insulin value (ng/mL) | | | |
|---|---|---|---|---|---|
| | | 0 min. | 30 min. | 90 min. | 180 min. |
| anesthesia | glucose +leucine | 137 ± 72 | 1717 ± 319 | 3826 ± 807 | 5731 ± 2471 |
| Non-anesthesia | glucose +leucine | 32 ± 26 | 1020 ± 229 | 386 ± 111 | 353 ± 100 |

Each value shows average value ± standard error.

It was observed that the serum insulin value of the parallel administration group with leucine under anesthesia increased for a lasting time during the maintenance of anesthesia and, in comparison with the parallel administration group of leucine, the serum insulin value increased 1.7 times in 30 minutes, 9.9 times in 90 minutes, and 16.2 times in 180 minutes.

This result shows that branched amino acid administration has the inhibiting effect on the blood sugar elevation observed when glucose was administered, and enhances the promotion of insulin secretion compared with the condition under non-anesthesia.

Test Example 7

Effect of Blood Sugar Decrease by Oral Administration of Leucine—comparison Between Anesthesia Condition and Non-Anesthesia condition—

Test Method

Non-anesthesia group: rats under overnight fasting conditions were divided into groups by body weight, and blood was collected from a tail vein (Pre Value). Shortly after that, 10 mL/kg of distilled water was orally administered to control group, and 0.3 g/10 mL/kg of leucine suspension to a sample solution group. Blood was collected from the tail vein 90 minutes after the administration of distilled water and the sample solution (90 minutes value).

Anesthesia group: rats under overnight fasting conditions were divided into groups by body weight, and blood was collected from a tail vein (Pre Value). After the blood collection, 10 mL/kg of distilled water was orally administered to a control group, and 0.3 g/10 mL/kg of leucine suspension to a sample solution group. Saflow indwelling needle was kept in the tail vein 30 minutes after the sample solution was administered. After that, anesthesia was introduced by rapid intravenous administration of 30 mg/kg Pentobarbital Sodium. Thereafter, a gastight syringe disposed in micro syringe pump and an indwelling needle were connected through an extension tube, and anesthesia was maintained by continuous intravenous administration of 30 mg/kg/hr. Blood was collected from the tail vein opposite to that wherein the indwelling needle was kept 60 minutes after introduction of anesthesia (90 minutes value).

In addition, blood was collected in a tube for hematocrit determination. After collected blood was centrifuged, plasma fraction was recovered and the blood sugar level was determined according to Test Example 1.

The changed value of the blood sugar level was calculated by deducting Pre value of each rat plasma from 90 minutes value of each rat plasma.

Figure 7:
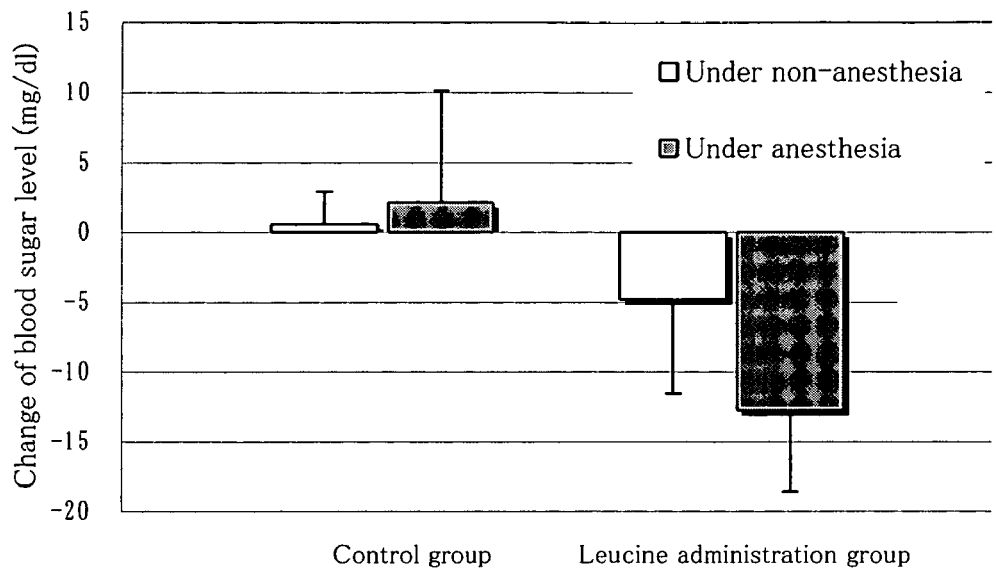
FIG. 7 shows an effect of leucine on blood sugar level under non-anesthesia and anesthesia.

The result of Test Example 7 is shown in FIG. 7. The significant elevation of blood sugar was not recognized 30 minutes after the administration between the control groups of non-anesthesia and anesthesia in comparison with before the start of administration. With respect to the sample solution groups of non-anesthesia and anesthesia, a decrease in blood sugar level was recognized in both of the groups, and the decrease extent of blood sugar level in the anesthesia group was 2.7 times compared to non-anesthesia group. Under anesthesia, i.e. in the perioperative period, it was revealed that branched amino acids are more able to lower the blood sugar level compared to under non-anesthesia condition.

Test Example 8

Inhibiting Effect of Blood Sugar Elevation by Oral Administration of Isoleucine During Sugar Tolerance—Comparison Between Under Non-Anesthesia and Anesthesia—

Test Method

Non-anesthesia group: rats under overnight fasting conditions were divided into groups by body weight, blood was collected from a tail vein (Pre Value). To a control group and a sample solution group was orally administered 0.5 g/10 mL/kg of OTSUKA distilled water (water for injection; manufactured by OTSUKA PHAMACEUTICAL FACTORY, INC.) and 0.5 g/10 mL/kg of aqueous isoleucine solution, respectively. 50% OTSUKA sugar solution (glucose injection (glucose 100 g/200 mL); manufactured by OTSUKA PHAMACEUTICAL FACTORY, INC.; hereinafter also simply called glucose solution) was administered orally so as to be 3 g glucose/kg 30 minutes after the administration of the sample solution. Blood was collected from the tail vein 30 minutes, 60 minutes, 90 minutes, and 120 minutes after the start of sugar solution administration, and the blood sugar level was determined. Each blood sugar level was considered as 30 minutes value, 60 minutes value, 90 minutes value, and 120 minutes value, respectively in the non-anesthesia group.

Anesthesia group: rats under overnight fasting conditions were divided into groups by body weight, blood was collected from a tail vein (Pre Value). To a control group and an isoleucine administration group were orally administered 0.5 g/10 mL/kg of OTSUKA distilled water and 0.5 g/10 mL/kg of aqueous isoleucine solution, respectively. 50% OTSUKA sugar solution was administered orally so as to be 3 g glucose/kg 30 minutes after the administration of the sample solution. To the anesthesia group was administered 0.5 g/1 mL/kg of Somnopentyl intraperitoneally from the abdominal cavity 10 minutes after the sugar solution administration. The blood sugar level of the blood collected from the tail vein 30 minutes, 60 minutes, 90 minutes, and 120 minutes after the administration of sugar solution was determined.

In addition, blood was collected in a tube for hematocrit determination. The collected blood was centrifuged to recover plasma. The fractionated plasma was served for the determination of the blood sugar level. Area under the blood sugar level curve (0-120 min; hereinafter abbreviated as AUC) was obtained by integrating the time (minutes) and the blood sugar level (mg/dL) at 5 points of 0 minutes value (which is Pre value), 30 minutes value, 60 minutes value, 90 minutes value, and 120 minutes value.

Figure 8:
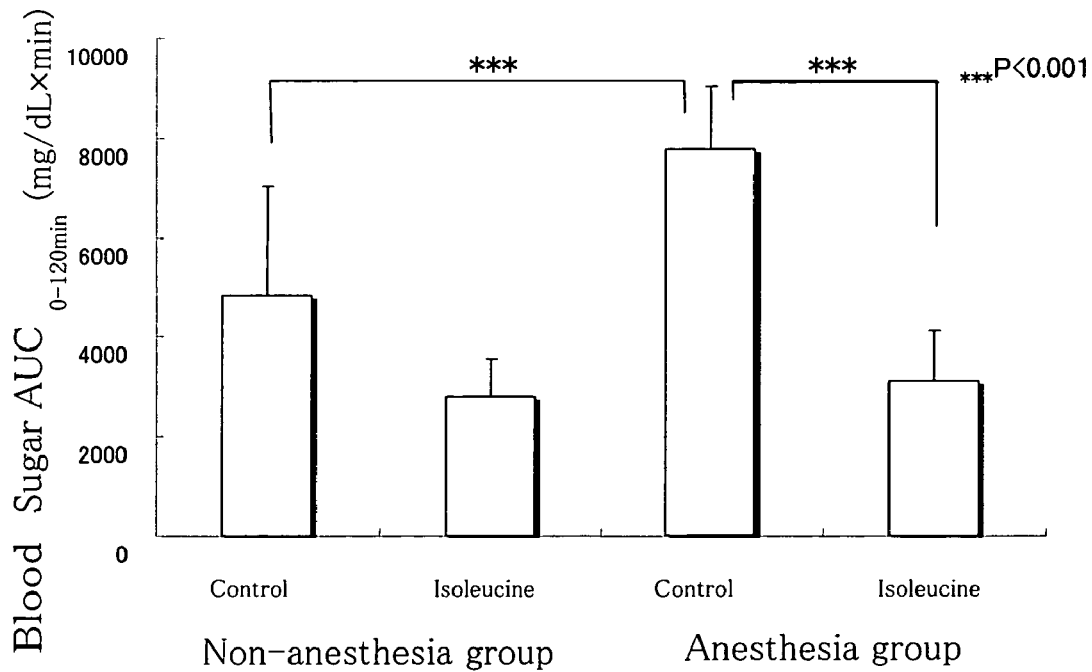
FIG. 8 shows an effect of isoleucine on AUC during sugar tolerance.

The result of Test Example 8 is shown in FIG. 8. With respect to the control groups, AUC of the anesthesia group is increased significantly compared to that of the non-anesthesia group. With respect to the isoleucine administration group, AUC of both non-anesthesia group and anesthesia group was decreased compared to that of the control group, and significant decrease was recognized in the anesthesia group. This result shows that the blood sugar elevation by sugar tolerance is significantly increased, and the inhibiting effect on the blood sugar elevation by oral administration of isoleucine is significantly enhanced by significant interaction between anesthetic agent and isoleucine.

Industrial Applicability

The inhibitor for blood sugar elevation of the present invention can inhibit the blood sugar elevation caused by surgery and anesthesia by administration to perioperative patients. Further, the inhibiting effect can be enhanced by placing patients under anesthesia. With respect to the above-mentioned inhibitor, its constituent components are branched amino acids, and the inhibitor has no risk of causing hypoglycemia which has been feared in the conventional insulin administration method for controling blood sugar level in the perioperative period. In addition, it is easy to perform saccharide supplementation to patients suffered from sugar metabolism disorders, at the time of surgery, and such inhibitor is safe to the living body including human.

The invention claimed is:

1. A method of inhibiting blood sugar elevation caused by an anesthetic agent administered to a perioperative patient under fasting condition, which comprises administering an inhibitor for blood sugar elevation consisting essentially of isoleucine, to the perioperative patient under fasting condition, wherein the inhibitor for blood sugar elevation contains 0.25 to 3.5 g/dL of isoleucine.

2. The method according to claim 1, wherein the inhibitor for blood sugar elevation contains 1 to 10 g/dL of glucose and 0.25 to 3.5 g/dL of isoleucine.

* * * * *